United States Patent [19]

Englert et al.

[11] Patent Number: 5,310,753
[45] Date of Patent: May 10, 1994

[54] ETHANOL ADDUCTS OF 6-SULFONYL-SUBSTITUTED 3-HYDROXY-CHROMANS AND THEIR USE AS INHALANTS IN DISEASES

[75] Inventors: Heinrich Englert, Hofheim am Taunus; Dieter Mania, Königstein am Taunus; Paul-Gerhard Kibat, Wiesbaden; Doris Gehring, Kelkheim; Erich Paulus, Eppstein/Taunus, all of Fed. Rep. of Germany

[73] Assignee: Hoechst Aktiengesellschaft, Frankfurt am Main, Fed. Rep. of Germany

[21] Appl. No.: 988,839

[22] Filed: Dec. 10, 1992

[30] Foreign Application Priority Data

Dec. 14, 1991 [DE] Fed. Rep. of Germany ....... 4141350

[51] Int. Cl.$^5$ ................... A61K 31/40; A61K 31/445; C07D 405/04
[52] U.S. Cl. ................... 514/422; 514/320; 546/196; 548/525
[58] Field of Search ............ 546/196; 548/525; 514/320, 422

[56] References Cited

U.S. PATENT DOCUMENTS 4,786,639 11/1988 Evans .................. 514/254
4,975,453 12/1990 Becker ................. 548/452
4,999,371 3/1991 Englert et al. .......... 514/422

FOREIGN PATENT DOCUMENTS

| 38189/89 | 1/1990 | Australia . |
| 176689 | 4/1986 | European Pat. Off. . |
| 0277612 | 8/1988 | European Pat. Off. . |
| 351270 | 1/1990 | European Pat. Off. . |
| 0351720 | 1/1990 | European Pat. Off. . |
| 0412760 | 2/1991 | European Pat. Off. . |
| PCT/GB85/-00588 | 7/1986 | PCT Int'l Appl. . |

Primary Examiner—C. Warren Ivy
Assistant Examiner—Celia Chang
Attorney, Agent, or Firm—Finnegan, Henderson, Farabow, Garrett & Dunner

[57] ABSTRACT

The invention relates to ethanol adducts of the compounds of the formula I

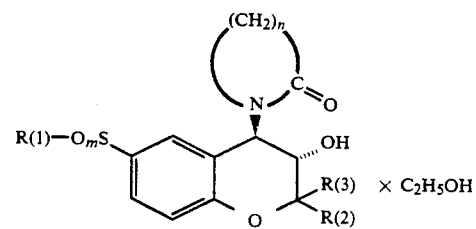

to a process for their preparation and to their use as inhalants in diseases, in particular in asthma.

6 Claims, No Drawings

ETHANOL ADDUCTS OF 6-SULFONYL-SUBSTITUTED 3-HYDROXY-CHROMANS AND THEIR USE AS INHALANTS IN DISEASES

The invention relates to ethanol adducts of the compounds of the formula I

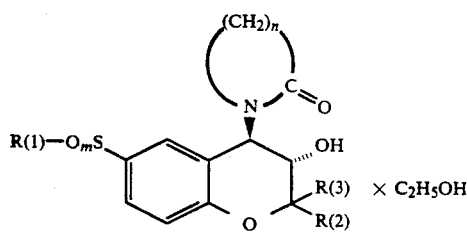

in which
R(1) is phenyl which can be substituted by 1 or 2 methyl groups and/or chlorine,
R(2) and R(3) are identical or different and are H, methyl or ethyl, and
n is the number 3 or 4,
and m is 1 or 2.

The invention relates exclusively to optically active compounds in which the lactam radical and the hydroxy group have the 4R- or the 3S-configuration. If the 2-carbon atom of the chroman system is asymmetrically substituted, the invention relates to compounds having either the S- or R-configuration.

Ethanol adducts are understood as meaning stable solvates of the compounds I with ethanol in the sense that ethanol is a solid consituent of the crystal lattice by means of which the particular compound is characterized in solid form.

Of the compounds I, the ethanol adduct of (3S,4R)-3-hydroxy-2,2-dimethyl-4-(2-oxo-1-pyrrolidinyl)-6-phenylsulfonylchroman is particularly preferred.

The base compounds of the formula Ia

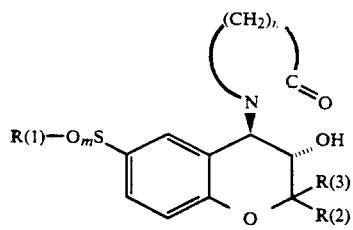

have already been disclosed in Patent Application EP 277,612, and their use in the treatment of asthma is described in Patent Application EP 351,720. It is a case there, however, not of ethanol adducts, but either of solvate-free compounds I or of their hydrates. In the applications of the compounds Ia proposed there, such as, for example, in asthma, in which the substances are preferably administered by inhalation, this is restricted, however, to atomization of solutions of the substances, for example of aqueous solutions. This can only be carried out in a restricted manner, however, with the very limited water solubility of the compounds Ia. Inhalation of the powdered substances, either directly or as a suspension thereof in chlorofluorohydrocarbon (CFC) as a propellant gas, which would permit a substantially higher and more rapid dosage, would be substantially more advantageous. In order to ensure a good lung accessibility of substances inhaled as powders, a micronization must be carried out in such cases. In this connection, it has been shown that substances according to EP 351,720 cannot be micronized or can only be micronized very incompletely using the customary grinding processes because of their inherent tackiness.

Surprisingly, it has now been possible to prepare for the compounds Ia their hitherto unknown ethanol adducts I. They prove to be stable and very readily micronizable, and they do not change their particle size in contrast to the substances disclosed in EP 351,720 if they are suspended in a CFC or related propellant. The ethanol adducts according to the invention thus have useful physical properties, which can be advantageously utilized in their application as powder inhalants.

Structurally similar compounds and their solvates, preferably their hydrates, and their application in asthma are also mentioned, for example, in EP Patent 176,689 without, however, unusual qualities of a solvate or even of an ethanol adduct for the preparation of a powder inhalant having been referred to or one of this type having ever been isolated and described.

The ethanol adducts according to the invention are prepared by bringing a solvate-free compound of the formula Ia or any desired other solvate of the compounds Ia, for example the hydrates, into contact with ethanol, preferably by recrystallizing such a compound from ethanol.

The synthesis of the starting materials required for such a conversion is described either in EP Application 277,612, or their preparation is carried out in an analogous manner to that shown for Example 1.

As already mentioned, the ethanol adducts are particularly suitable for an inhalation application, for example in obstructive airway diseases, such as asthma. The daily dose here, in the case of asthma, is about 0.1 $\mu g/kg$ of body weight to about 100 $\mu g/kg$, depending on the severity of the disease, a range from 1–10 $\mu g/kg$ being particularly preferred. For an inhalation application, the ethanolate is made available as a micronized powder, a particle size of at least 10 $\mu m$, but preferably from 3–8 $\mu m$, being advantageous. Such a powder is either inhaled as such with or without addition of auxiliaries, such as, for example, lactose, or inspired with the respiratory air, using a suitable apparatus. It can also be used, however, in a propellant gas preparation, for example in a metered aerosol pressurized container, where additives—such as surface-active substances or other additions—may be needed.

EXAMPLE 1

(3S,4R)-3-Hydroxy-2,2-dimethyl-4-(2-oxo-1-pyrrolidinyl)-6-phenylsulfonylchroman ethanolate adduct (3S,4R)-3-Hydroxy-2,2-dimethyl-4-(2-oxo-1-pyrrolidinyl)-6-phenylsulfonylchroman hemihydrate is dissolved in boiling ethanol and slowly cooled to room temperature. The product is dried at 80° C. for 8 h. M.p.118°–120° C.; IR (KBr, cm$^{-1}$) 1639, 1480, 1302, 1152, 1080, 941, 732, 608, 577; analysis calc. for $C_{21}H_{23}NO_5 \times 1\ C_2H_5OH$: C, 61.7; H, 6.5; N, 3.1; found: C, 61.5; H, 6.3; N, 3.2.

Preparation of the starting material (3S,4R)-3-hydroxy-2,2-dimethyl-4-(2-oxo-1-pyrrolidinyl)-6-phenylsulfonylchroman hemihydrate 13.2 g (0.03 mol) of (3S,4R)-4-(4-chlorobutyrylamino)-3-hydroxy-2,2-dimethyl-6-phenylsulfonylchroman are dissolved in 100 ml of THF and treated with 4 g of finely ground solid NaOH. The reaction mixture is stirred at room temperature for one hour and concentrated in vacuo after addition of 25 ml of $H_2O$. The residue is treated with ice water until crystallization starts. Recrystallization from pure methanol and subsequently from methanol/$H_2O$ (1:2) gives the hemihydrate adduct.

Yield: 10.0 g, m.p. 121°–123° C., $^1$H-NMR (270 MHz, $CDCl_3$): 1.25 (s, $CH_3$), 1.51 (s, $CH_3$), 2.00–2.18 (m, C(4')$H_2$), 2.47–2.70 (m, C(3')$H_2$), 2.95–3.05 (m, C(5')$H_2$), 3.18–3.30 (ps-dd, C(5')$H_2$), 3.13 (d, J=5.6 Hz, O—H), 3.71 (dd, J=10 Hz, J'=5.6 Hz, C(3)$H_2$), 5.31 (d, J=10 Hz, C(4)$H_2$), 6.91 (d, J=8.4 Hz, C(6)$H_2$), 7.45–7.60, 7.73, 7.9 (m, 7H, Ar—H); $[\alpha]_D^{20} = +41°$ (c=1, ethanol), IR (KBr, cm$^{-1}$) 1663, 1478, 1320, 939, 602; analysis calc. for $C_{21}H_{23}NO_5 \times 0.5\ H_2O$: C, 61.4; H, 5.9; N, 3.4; found: C, 61.4; H, 5.7; N, 3.4.

Preparation of Other Precursors (3S,4R)-4-(4-Chlorobutyrylamino)-3-hydroxy-2,2-dimethyl-6-phenylsulfonylchroman 15.8 g (0.033 mol) of (3S,4R)-4-amino-3-hydroxy-2,2-dimethyl-6-phenylsulfonylchroman (+)-mandelate are added to a stirred mixture of 3.26 g of NaOH in 80 ml of $H_2O$ and 80 ml of $CH_2Cl_2$. After cooling to 5° C., 6.84 g (0.0485 mol) of 4-chlorobutyryl chloride are added and the mixture is stirred for a further 30 min at 5°–10° C. After addition of 100 ml of $CH_2Cl_2$ (in order to bring already precipitated product into solution again), the organic phases are separated off and washed twice with 2N NaOH and subsequently with $H_2O$. After evaporation of the solvent, the residue is treated with hot diisopropyl ether.

Yield: 13.6 g; m.p.: 178–180; $[\alpha]_D^{20} = -25°$ (c=1, methanol), analysis calc. for $C_{21}H_{24}ClNO_5S$: C, 57.6; H, 5.5; N, 3.2; found: C, 57.4; H, 5.5; N, 3.2.

(3S,4R)-4-Amino-3-hydroxy-2,2-dimethyl-6-phenylsulfonylchroman (+)-mandelate and free base 198 g (0.59 mol) of racemic 4-amino-3-hydroxy-2,2-dimethyl-6-phenylsulfonylchroman and 90.28 g (0.59 mol) of (+)-mandelic acid are dissolved in 4.5 l of hot (60° C.) absolute ethanol. The mixture is allowed to cool to room temperature in the course of 2 h. If spontaneous crystallization does not occur during the course of this, the solution is seeded with 0.3 g of the optically pure final product. The solution is then left at room temperature for 48 h and the crystals obtained are filtered off with suction. The material thus obtained of $[\alpha]_D^{20} = +83.6°$ (c=1, DMF) is again boiled under reflux for 1 h in 1 l of ethanol and after cooling gives homogeneous (+)-mandelate.

Yield: 81 g; m.p.: 203°–204° C.; $[\alpha]_D^{20} = +94°$ (c=1, DMF); analysis calc. for $C_{25}H_{27}NO_7S$: C, 61.8; H, 5.6; N, 2.9; found: C, 62.1; H, 5.7; N, 3.0.

The corresponding free base was obtained by suspending the mandelate in a stirred mixture of 2N NaOH and $CH_2Cl_2$.

$[\alpha]_D^{20} = +86°$ (c=1, DMF).

4-Amino-3-hydroxy-2,2-dimethyl-6-phenylsulfonylchroman 50 g (0.158 mol) of 3,4-epoxy-2,2-dimethyl-6-phenylsulfonylchroman, dissolved in 280 ml of ethanol, are shaken in an autoclave at 70° C. and under an $NH_3$ pressure of 7 bar for 18 h. After evaporating the solvent, the residue is recrystallized from isopropanol. Yield: 39.9 g; m.p.: 166°–167° C.

3,4-Epoxy-2,2-dimethyl-6-phenylsulfonylchroman

To 100 ml of absolute DMSO are added 1.8 g (0.06 mol) of NaH as an 80% strength suspension in oil and, dropwise, 20 g of 3-bromo-4-hydroxy-2,2-dimethyl-6-phenylsulfonylchroman, dissolved in 80 ml of DMSO, the reaction temperature being kept at 25°–28° C. After stirring at room temperature for 2 hours, the mixture is stirred into ice water and the resulting precipitate is filtered off with suction. Further purification can be achieved by dissolving the crude product in ethyl acetate and treating it with active carbon. After evaporating the solvent, the residue is treated with diisopropyl ether until crystallization starts. Yield: 14.5 g; m.p.: 103°–105° C.

3-Bromo-4-hydroxy-2,2-dimethyl-6-phenylsulfonylchroman

To 200 g of 4-nitrodiphenylsulfone (0.76 mol) and 140 ml (1.45 mol) of 2-methyl-3-butyn-3-ol in 1.4 l of DMSO are added 100 g of solid NaOH platelets. The mixture is stirred at room temperature for 5 h, a further 50 ml of 2-methyl-3-butyn-3-ol being added after a stirring time of 2 h. The mixture is then stirred into 1.5 l of diisopropyl ether and 1 l of $H_2O$. The organic phase is separated off and washed 3 times with $H_2O$. After evaporating the solvent, a reddish oil remains. A small sample can be obtained pure by chromatography on silica gel: 2-methyl-3-(4-phenylsulfonyl)phenoxy-3-butyne, m.p.: 58°–60° C.; analysis calc. for $C_{17}H_{16}O_3S$: C, 68.0; H, 5.4; found: C, 67.5; H, 5.8.

The major amount of this product is dissolved in 800 ml of 1,2-dichlorobenzene without further purification and heated under reflux for 2 h. After distilling off the solvent in vacuo at 100° C., a dark oil is obtained which can likewise be purified by chromatography on silica gel to give pure 2,2-dimethyl-6-phenylsulfonylchromene, m.p.: 95°–96° C.; analysis calc. for $C_{17}H_{16}O_3S$: C, 68.0; H, 5.4; found: C, 68.3; H, 5.3.

The crude product obtained from this compound is dissolved in 600 ml of DMSO and 10 ml of $H_2O$ and treated at 15° C. with 100.2 g of N-bromosuccinimide, divided into small portions. The mixture was stirred for a total of 5 h and then poured into ice water. Extraction with methyl tert-butyl ether gives crude 3-bromo-4-hydroxy-2,2-dimethyl-6-phenylsulfonylchroman, which is obtained pure by stirring in diisopropyl ether. Yield over 3 steps: 105.3 g; m.p.: 122°–124° C.

Pharmacological Data a) Micronization 890 g of (3S,4R)-3-hydroxy-2,2-dimethyl-4-(2-oxo-1-pyrrolidinyl)-6-phenylsulfonylchroman are micronized in an air-jet mill. The particle size was <10 μm for 50% of the particles. With (3S,4R)-3-hydroxy-2,2-dimethyl-4-(2-oxo-1-pyrrolidinyl)-6-phenylsulfonylchroman or (3S,4R)-3-hydroxy-2,2-dimethyl-4-(2-oxo-1-pyrrolidinyl)-6-phenylsulfonylchroman hemihydrate no grinding could be carried out under these conditions, since the substances gummed up the carrying passages of the mill.

b) Stability in CFC

The micronized material from (3S,4R)-3-hydroxy-2,2-dimethyl-4-(2-oxo-1-pyrrolidinyl)-6-phenylsulfonyl-chroman ethanolate adduct obtained in a) did not change its particle size when it was suspended in a CFC for 8 days.

c) Bronchodilating Action in Anesthetized Guinea Pigs

The micronized material from (3S,4R)-3-hydroxy-2,2-dimethyl-4-(2-oxo-1-pyrrolidinyl)-6-phenylsulfonyl-chroman ethanolate adduct obtained in a) is suspended in CFC and sealed into a pressurized aerosol metering container. The concentration is chosen such that per spray burst an amount of substance of 0.1 mg or 1.0 mg is sprayed with about 0.5 ml of CFC. If such a spray burst is introduced into the inhalation tubing of the respiratory pump of a pentobarbital-anesthetized guinea pig dissected by the Konzett-Rössler method, there is a reduction in the bronchoconstriction induced by histamine i.v. lasting for 30 minutes (n=2) or 40 min (n=3), complete inhibition initially being observed. The details of the method were carried out a described in EP 351,720.

We claim:
1. A crystalline ethanol adduct of the formula I

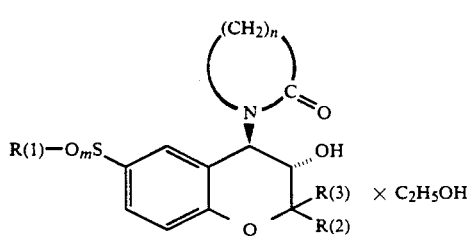

in which
R(1) is phenyl which can be substituted by 1 or 2 methyl groups, a chlorine group or both methyl and chlorine groups,
R(2) and R(3) are identical or different and are hydrogen, methyl or ethyl,
n is the number 3 or 4,
and m is 1 or 2.
2. A crystalline ethanol adduct as in claim 1 wherein said crystalline ethanol adduct of the formula I is (3S,4R)-3-hydroxy-2,2-dimethyl-4-(2-oxo-1-pyrrolidinyl)-6-phenylsulfonylchroman ethanolate adduct.

3. A method of treating asthma comprising administering an ethanol adduct of the formula I

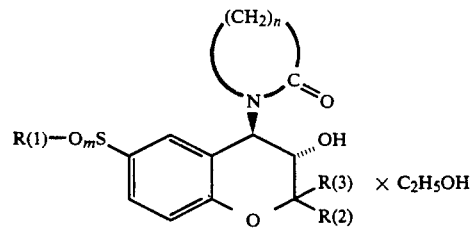

in which
R(1) is phenyl which can be substituted by 1 or 2 methyl groups, a chlorine group or both methyl and chlorine groups,
R(2) and R(3) are identical or different and are hydrogen, methyl or ethyl,
n is the number 3 or 4,
and m is 1 or 2;
as an inhalant to a patient for the treatment of asthma.
4. A medicament comprising an effective amount of an ethanolate of the formula I

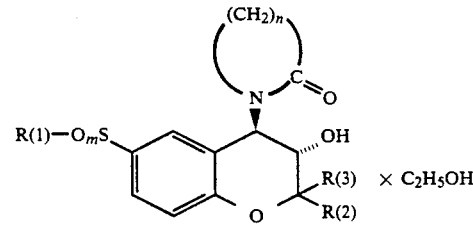

in which
R(1) is phenyl which can be substituted by 1 or 2 methyl groups, a chlorine group or both methyl and chlorine groups,
R(2) and R(3) are identical or different and are hydrogen, methyl or ethyl,
n is the number 3 or 4,
and m is 1 or 2;
and at least one pharmaceutically customary additive.
5. An method of treating asthma as in claim 3, wherein said ethanol adduct of the formula I is (3S,4R)-3-hydroxy-2,2-dimethyl-4-(2-oxo-1-pyrrolidinyl)-6-phenylsulfonylchroman ethanolate adduct.
6. A medicament as in claim 4, wherein said ethanolate of the formula I is (3S,4R)-3-hydroxy-2,2-dimethyl-4-(2-oxo-1-pyrrolidinyl)-6-phenylsulfonylchroman ethanolate adduct.

* * * * *